(12) United States Patent
Keller

(10) Patent No.: US 8,905,760 B2
(45) Date of Patent: Dec. 9, 2014

(54) METHODS AND SYSTEMS FOR PROGRESSIVELY TREATING AND CONTROLLING ORAL PERIOPATHOGENS CAUSING SYSTEMIC INFLAMMATIONS

(76) Inventor: Duane C. Keller, St. Louis, MO (US)

(*) Notice: Subject to any disclaimer, the term of this patent is extended or adjusted under 35 U.S.C. 154(b) by 667 days.

(21) Appl. No.: 12/417,458

(22) Filed: Apr. 2, 2009

(65) Prior Publication Data

US 2010/0112525 A1    May 6, 2010

Related U.S. Application Data

(63) Continuation-in-part of application No. 12/264,765, filed on Nov. 4, 2008.

(51) Int. Cl.
*A61C 15/00* (2006.01)
*A61C 19/06* (2006.01)

(52) U.S. Cl.
CPC ............. *A61C 19/063* (2013.01); *A61C 19/066* (2013.01)
USPC ........................................... 433/216; 433/215

(58) Field of Classification Search
CPC ............................... A61C 19/063; A61Q 11/00
USPC ...................... 433/215–216, 229; 424/49–58; 514/900, 902
See application file for complete search history.

(56) References Cited

U.S. PATENT DOCUMENTS

| | | | |
|---|---|---|---|
| 4,514,382 A | 4/1985 | Gaffar et al. | |
| 4,568,535 A | 2/1986 | Loesche | |
| 4,569,837 A | 2/1986 | Suzuki et al. | |
| 4,670,252 A | 6/1987 | Sampathkumar | |
| 4,701,320 A | 10/1987 | Hasegawa et al. | |
| 4,751,051 A | 6/1988 | Thompson et al. | |
| 4,819,158 A | 4/1989 | Miyashita | |
| 4,842,846 A | 6/1989 | Nakano | |
| 4,892,736 A | 1/1990 | Goodson | |
| 4,906,670 A | 3/1990 | Higashi et al. | |
| 4,916,193 A | 4/1990 | Tang et al. | |
| 4,933,182 A | 6/1990 | Higashi et al. | |
| 4,963,347 A | 10/1990 | Humphries et al. | |
| 4,966,774 A | 10/1990 | Nakano et al. | |
| 4,975,271 A | 12/1990 | Dunn et al. | |

(Continued)

OTHER PUBLICATIONS

Ximenez-Fyvie, et al. "Microbial Composition of supra- and subgingival plaque in subjects with adult periodontitis", 2000, Journal of Clinical Periodontol: 27: 722-732.*

(Continued)

*Primary Examiner* — Edward Moran
(74) *Attorney, Agent, or Firm* — Polster Lieder

(57) ABSTRACT

Methods and systems for treating and controlling oral periopathogens that have been found to be associated with systemic inflammation and/or disease in a periodontal pocket, inhibiting their entry into the host circulatory system, and decreasing the systemic effects. A bacterial community present in one or more oral treatment regions is determined. A periodontal medicament delivery tray is prepared for the patient with the delivery tray being configured with one or more application regions, each configured for applying a medicament to a different one of the oral treatment regions. The medicaments are applied to each oral treatment region, including placing each medicament into a different application region of the delivery tray. Each of the applied medicaments is applied as a function of a determined efficacy of the medicament against the bacterial community determined to be in the oral treatment region associated with the application region in which each medicament is applied.

32 Claims, 9 Drawing Sheets

(56) References Cited

U.S. PATENT DOCUMENTS

| | | | |
|---|---|---|---|
| 4,980,152 A | 12/1990 | Frazier et al. |
| 4,985,235 A | 1/1991 | Kligman |
| 4,990,329 A | 2/1991 | Sampathkumar |
| 5,032,384 A | 7/1991 | Yeh et al. |
| 5,057,497 A | 10/1991 | Calam et al. |
| 5,087,451 A | 2/1992 | Wilson et al. |
| 5,110,583 A | 5/1992 | Sampathkumar |
| 5,129,824 A | 7/1992 | Keller |
| 5,160,737 A | 11/1992 | Friedman et al. |
| 5,176,901 A | 1/1993 | Gallopo et al. |
| 5,188,817 A | 2/1993 | Ozick |
| 5,217,710 A | 6/1993 | Williams et al. |
| 5,240,710 A | 8/1993 | Bar-Shalom et al. |
| 5,277,908 A | 1/1994 | Beckman et al. |
| 5,330,357 A | 7/1994 | Keller |
| 5,340,566 A | 8/1994 | Curtis et al. |
| 5,372,802 A | 12/1994 | Barrows et al. |
| 5,374,418 A | 12/1994 | Oshino et al. |
| 5,409,703 A | 4/1995 | McAnalley et al. |
| 5,419,703 A | 5/1995 | Warrin et al. |
| 5,438,076 A | 8/1995 | Friedman et al. |
| 5,472,684 A | 12/1995 | Nabi et al. |
| 5,599,553 A | 2/1997 | Chung |
| 5,605,676 A | 2/1997 | Gaffar et al. |
| 5,607,681 A | 3/1997 | Galley et al. |
| 5,607,686 A | 3/1997 | Totakura et al. |
| 5,616,313 A | 4/1997 | Williams et al. |
| 5,632,972 A | 5/1997 | Williams et al. |
| 5,639,795 A | 6/1997 | Friedman et al. |
| 5,648,399 A | 7/1997 | Friedman et al. |
| 5,701,320 A | 12/1997 | Sugiyama et al. |
| 5,709,873 A | 1/1998 | Bar-Shalom et al. |
| 5,730,995 A | 3/1998 | Shirono et al. |
| 5,800,803 A | 9/1998 | Mirajkar et al. |
| 5,817,294 A | 10/1998 | Arnold |
| 5,820,841 A | 10/1998 | Chen et al. |
| 5,827,503 A | 10/1998 | Schwabe |
| 5,885,553 A | 3/1999 | Michael |
| 5,906,811 A | 5/1999 | Hersh |
| 5,908,613 A | 6/1999 | Bozzacco |
| 5,908,614 A | 6/1999 | Montgomery |
| 5,928,187 A | 7/1999 | Glukhov et al. |
| 5,939,080 A | 8/1999 | Michael et al. |
| 5,998,487 A | 12/1999 | Brahms et al. |
| 6,049,002 A | 4/2000 | Mattila et al. |
| 6,080,712 A | 6/2000 | Revell et al. |
| 6,153,210 A | 11/2000 | Roberts et al. |
| 6,200,550 B1 | 3/2001 | Masterson et al. |
| 6,228,347 B1 | 5/2001 | Hersh |
| 6,228,354 B1 | 5/2001 | Jeng |
| 6,232,340 B1 | 5/2001 | Zhang et al. |
| 6,247,930 B1 | 6/2001 | Chiang et al. |
| 6,290,934 B1 | 9/2001 | Kramer et al. |
| 6,314,960 B1 | 11/2001 | Vines |
| 6,325,991 B1 | 12/2001 | Draheim |
| 6,409,992 B1 | 6/2002 | Kleinberg et al. |
| 6,416,745 B1 | 7/2002 | Markowitz et al. |
| 6,610,274 B1 | 8/2003 | Gardner |
| 6,682,722 B2 | 1/2004 | Majeti et al. |
| 6,685,921 B2 | 2/2004 | Lawlor |
| 6,692,727 B1 | 2/2004 | Yue et al. |
| 6,764,690 B2 | 7/2004 | Ahola et al. |
| 6,776,979 B2 | 8/2004 | Frager et al. |
| 6,929,790 B2 | 8/2005 | Kleinberg et al. |
| 6,966,773 B2 * | 11/2005 | Keller .............................. 433/80 |
| 7,018,622 B2 | 3/2006 | Goodhart et al. |
| 7,025,950 B2 | 4/2006 | Majeti et al. |
| 7,094,431 B2 | 8/2006 | Peshoff |
| 7,150,884 B1 | 12/2006 | Hilgren et al. |
| 7,190,884 B2 | 3/2007 | Fujiwara et al. |
| 2004/0019110 A1 | 1/2004 | Van Dyke et al. |
| 2004/0091432 A1 | 5/2004 | Dulin |
| 2004/0097432 A1 | 5/2004 | Roh-Schmidt et al. |
| 2004/0126440 A1 | 7/2004 | Frager et al. |
| 2004/0265396 A1 | 12/2004 | Peshoff |
| 2005/0203587 A1 | 9/2005 | Liebergesell |
| 2006/0034782 A1 | 2/2006 | Brown et al. |
| 2006/0036194 A1 | 2/2006 | Schultheiss et al. |
| 2006/0093561 A1 | 5/2006 | Kennedy |
| 2006/0182813 A1 | 8/2006 | Holladay |
| 2006/0257331 A1 | 11/2006 | Dulin |
| 2006/0271148 A1 | 11/2006 | Liebergesell et al. |
| 2007/0122490 A1 | 5/2007 | Peshoff |

OTHER PUBLICATIONS

"Antibiotics". Accessed at http://www.emedicinehealth.com on Nov. 4, 2011.*

Port, Tami. "How do Antibiotics Work to Kill Bacteria?". Oct. 2008. Accessed at http://www.tami-port.suite101.com/how-do-antibiotics-work-to-kill-bacteria-a74616 on Nov. 4, 2011.*

Feres et. al. Antibiotics in the Treatment of Periodontal Diseases: Microbiological Basis and Clinical Applications. Ann Roy Australas Coll Dent Surg, Jun. 2008; 19:37-44; p. 40, col. 2, para 4; p. 41, col. 1, para 1.

Kolenbrander et al. Communication among Oral Bacteria. Microbiol. Mol. Biol. Rev. 2002, 66(3): 486-505; p. 486, col. 2, para 3; p. 487, col. 1 para 1; p. 488, col. 2, para 1; p. 489, col. 1, para 1; p. 497, col. 1, para 1-2.

* cited by examiner

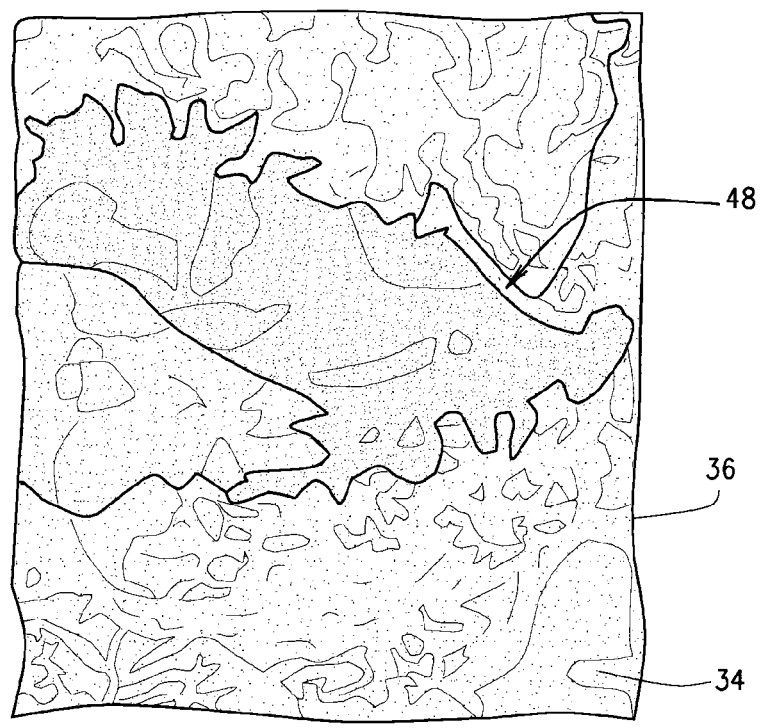
F I G . 5B

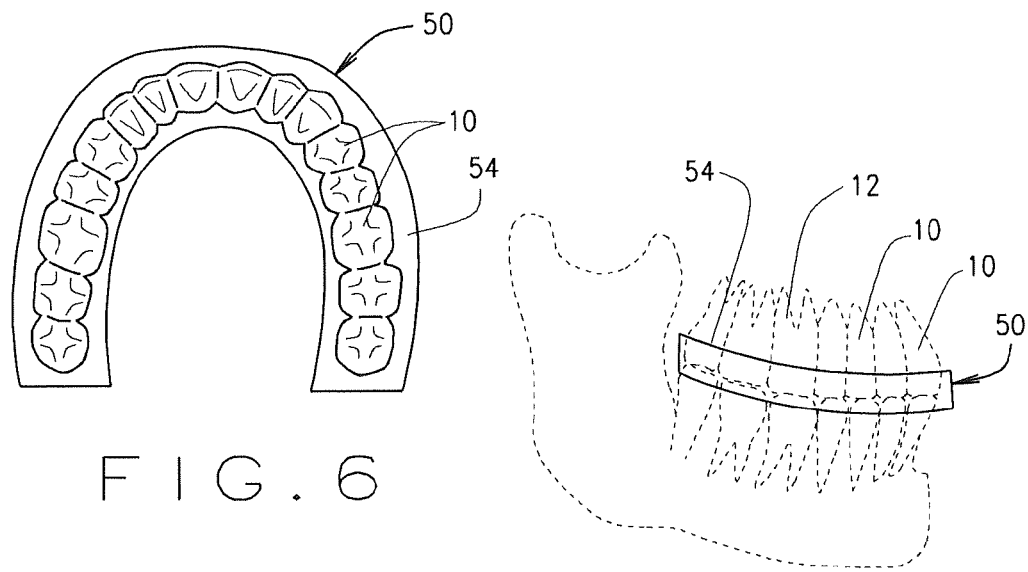
FIG. 6
FIG. 7
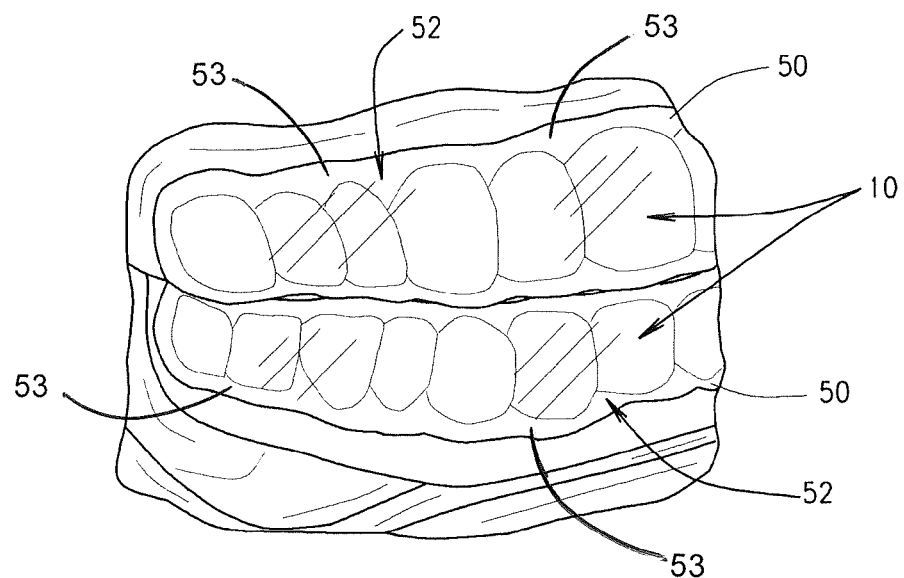
FIG. 8

METHODS AND SYSTEMS FOR PROGRESSIVELY TREATING AND CONTROLLING ORAL PERIOPATHOGENS CAUSING SYSTEMIC INFLAMMATIONS

CROSS-REFERENCE TO RELATED APPLICATIONS

This application is a continuation-in-part of U.S. patent application Ser. No. 12/264,765 filed on Nov. 4, 2008. The disclosure of the above application is incorporated herein by reference.

FIELD

The present disclosure relates to treatment of periodontal disease and, more specifically, to systems and methods for treating and controlling oral periopathogens that cause system inflammations.

BACKGROUND

The statements in this section merely provide background information related to the present disclosure and may not constitute prior art.

Medical research has demonstrated a significant source of systemic disease is related to specific oral bacteria, with special emphasis on certain gram negative anaerobic bacteria that have been found associated with a variety of systemic inflammatory responses and appear to originate only in periodontal pockets and enter the bloodstream through a close proximity to the host circulatory system. There are very few regions of the body which can readily be rendered conducive to the growth of anaerobic bacteria. Deeper periodontal pockets are one region that readily demonstrates infections that are predominantly anaerobic, with gram-negative bacteria being the most common isolates. The anatomic closeness of these biofilm periopathogens to the bloodstream can facilitate bacteremia and systemic spread of bacterial products, components, and immunocomplexes (antigen/antibody reactions, chemokines and cytokines).

It has been found that these oral periopathogens can become systemic. Research has demonstrated that bacteremia was observed in 100% of the patients after dental extraction and in 70% after dental scaling. Mastication on infected gum tissues increases systemic bacterial endotoxins levels four-fold. Simple oral hygiene procedures, such as brushing of the teeth, can increase the prevalence of bacteremia from 17 to 40%. Research has also demonstrated that the dissemination of oral microorganisms into the bloodstream is common. In fact, it has been found that within less than 1 minute after an oral procedure, organisms from an infected site can reach the heart, lungs, and peripheral blood capillary system of a patient. These periopathogens can cause host injury (exotoxins and toxic bacterial products), inflammation (immune system—antigen/antibody reactions) and infections (bacteremia) in a person. Periodontitis may affect the host's susceptibility to systemic disease in three ways: by shared risk factors, by subgingival biofilms acting as reservoirs of bacteria, and through the periodontium acting as a reservoir of inflammatory mediators.

It has also been found that controlling these periopathogens in the mouth decreases systemic responses. Studies have evaluated periodontitis and C-reactive protein (CRP) levels in patients. For example, one study evaluated three groups: (1) an untreated control group of 24 subjects; (2) a group of 21 subjects with a standard regimen of periodontal therapy (SPT), consisting of subgingival mechanical instrumentation; and (3) a group of 20 subjects who had an intensive course of periodontal treatment (IPT), consisting of SPT with adjunctive local delivery of minocycline-HCl (Arestin®, Orapharma, Warminster, Pa., USA). The results of this study in both treatment groups identified a considerable reduction of periodontal lesions after therapy [60±27 ($P<0.0001$, $N=21$) and 60±23 ($P<0.0001$, $N=20$) mean differences tested by t test, respectively]. No changes were observed in the untreated controls. Similar results were found in the IL-6 markers. The report of that study concluded that periodontitis causes moderate systemic inflammation in systemically healthy patients because reducing the periodontal disease resulted in a reduction in the systemic inflammatory markers.

Periodontitis is an infection that can stimulate the liver to produce C-reactive protein (CRP) (a marker of inflammation), which in turn will form deposits on injured blood vessels. CRP binds to cells that are damaged and fixes complement, which activates phagocytes, including neutrophils. These cells release nitric oxide, thereby contributing to atheroma formation. It has been found that patients with adult periodontitis have higher levels of CRP and haptoglobin than subjects without periodontitis. Both CRP and haptoglobin levels decline significantly after periodontal therapy. Additionally, in another study of 153 systemically healthy subjects consisting of 108 untreated periodontitis patients and 45 control subjects, the mean plasma CRP levels were higher in the periodontitis patients. Patients with severe periodontitis had significantly higher CRP levels than mild-periodontitis patients, and both had significantly higher levels than the controls. Another recent study evaluated the relationship of cardiovascular disease and CRP into three groups of adults: i) had neither periodontal nor cardiovascular disease, ii) had only one of these two diseases, and iii) had both of two diseases. In those with both heart disease and periodontal disease, the mean level of CRP (8.7 g/ml) was significantly different from that (1.14 g/ml) in controls with neither disease. It was also shown in that study that treatment of the periodontal disease caused a 65% reduction in the level of CRP within 3 months of treatment.

However, current methods to treat periodontal disease and the resulting effects thereof suffer from a number of significant drawbacks and are often ineffective in addressing the systemic effects of periodontal originated disease. Many of the systemic biomarkers decrease following conventional oral disinfection, but these biomarker decreases are short lived and return to abnormal elevated pre-treatment levels. The inventor of the present methods and systems has identified a significant need and desired benefit to many patients in developing new procedures and systems that address the systemic effects of periodontal originated diseases.

SUMMARY

The inventor hereof has succeeded at designing methods and systems for treating and controlling oral periopathogens in patients that provide enhancements and unexpected benefits to patients that are often beyond preventing periodontal disease and loss of gums and teeth.

In one aspect, a method of treating and controlling oral periopathogens includes performing an evaluation examination of a patient. The evaluation examination includes evaluating one or more treatment regions having potential periopathogens and determining a bacterial community and biofilm present in each treatment region. The method also includes preparing a periodontal medicament delivery tray having one or more application regions including one or more tooth indentations. Each application region is configured for applying one or more medicaments to a different one of the treatment regions. The method also includes selecting the a medicament to be applied to each of the treatment regions from among a plurality of potential medicaments capable of controlling the determined bacterial within the determined biofilm as determined to be in a particular treatment region. The selected medicament is applied to each treatment region and includes placing the medicament in the application region of the delivery tray associated with the particular treatment region for which the medicament was selected.

In another aspect, a method of treating and controlling oral periopathogens, includes determining a bacterial community and biofilm present in one or more oral treatment regions of a patient and preparing a periodontal medicament delivery tray for the patient. The delivery tray has one or more application regions including one or more tooth indentations. Each application region is configured for applying one or more medicaments to a different one of the treatment regions. A medicament is selected to be applied to each of the treatment regions from among a plurality of potential medicaments capable of controlling biofilm entities. The selection of the medicament is made as a function of the medicament's efficacy against the determined bacterial community and biofilm in the corresponding oral treatment region. The selected medicament is applied to each corresponding treatment region including placing the selected medicaments in an application region of the delivery tray corresponding to the oral treatment regions for which the medicament was selected based on efficacy.

In yet another aspect, a system for treating and controlling oral periopathogens includes means for determining a bacterial community present in one or more oral treatment regions of a patient and means for preparing a periodontal medicament delivery tray for the patient. The delivery tray is being configured with one or more application regions each configured for applying a medicament to a different one of the oral treatment regions. The systems also includes means for applying medicaments to each of the oral treatment regions, including placing each of the medicaments in a different application regions of the delivery tray, wherein each applied medicaments is applied as a function of a determined efficacy of the medicament against the bacterial community determined to be in the oral treatment region associated with the application region in which each medicament is applied.

In still another aspect, a method of controlling periopathogens that have been found to be associated with systemic inflammation and/or disease in a periodontal pocket, inhibiting their entry into the host circulatory system, and decreasing the systemic effects. A bacterial community present in one or more oral treatment regions is determined. A periodontal medicament delivery tray is prepared for the patient with the delivery tray being configured with one or more application regions each configured for applying a medicament to a different one of the oral treatment regions. The medicaments are applied to each of the oral treatment regions, including placing each of the medicaments in a different application region of the delivery tray. Each of the applied medicaments is applied as a function of a determined efficacy of the medicament against the bacterial community determined to be in the oral treatment region associated with the application region in which each medicament is applied.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIG. 5B is a line drawing representation of the photographic image of FIG. 5A.

FIG. 6 is a top plan view of a periodontal medicament delivery tray suitable for use with one or more embodiments of the present disclosure.

FIG. 7 is a side elevational view of a periodontal medicament delivery tray as worn by a patient for use in one or more embodiments of the treatments of the present disclosure.

FIG. 8 is a side elevational view of upper and lower periodontal medicament delivery trays as worn by a patient for simultaneous treatment of both the upper and lower teeth and associated marginal gingiva according to some embodiments.

It should be understood that throughout the drawings, corresponding reference numerals indicate like or corresponding parts and features.

DETAILED DESCRIPTION

The following description is merely exemplary in nature and is not intended to limit the present disclosure or the disclosure's applications or uses. Before turning to the figures and the various exemplary embodiments illustrated therein, a detailed overview of various embodiments and aspects is provided for purposes of breadth of scope, context, clarity, and completeness.

Periodontal disease has been found to be caused by planktonic bacteria or bacterium and/or micro-organisms living in a biofilm. The most virulent of these bacteria have inherent properties that include being gram negative-obligate anaerobes. These gram negative obligate anaerobic bacteria live in a biofilm in the deeper periodontal pockets and are therefore harder to reach or eliminate by conventional means. The bacterial biofilm matrix composed of lipopolysaccharides, exopolysaccharides and other surface products as well as the endotoxins, exotoxins and other bacterial products cause significant immune system responses. In addition, these gram negative-obligate anaerobes have been found to invade the tissues causing localized and systemic inflammatory responses and to invade the individual cells and are then impervious to the host immune system. The anaerobes as part of a biofilm are almost impervious to conventional treatments. Other micro-organisms, some of which may not yet be discovered, can be impervious to existing treatment modalities and can cause local and systemic effects.

Figure 1:
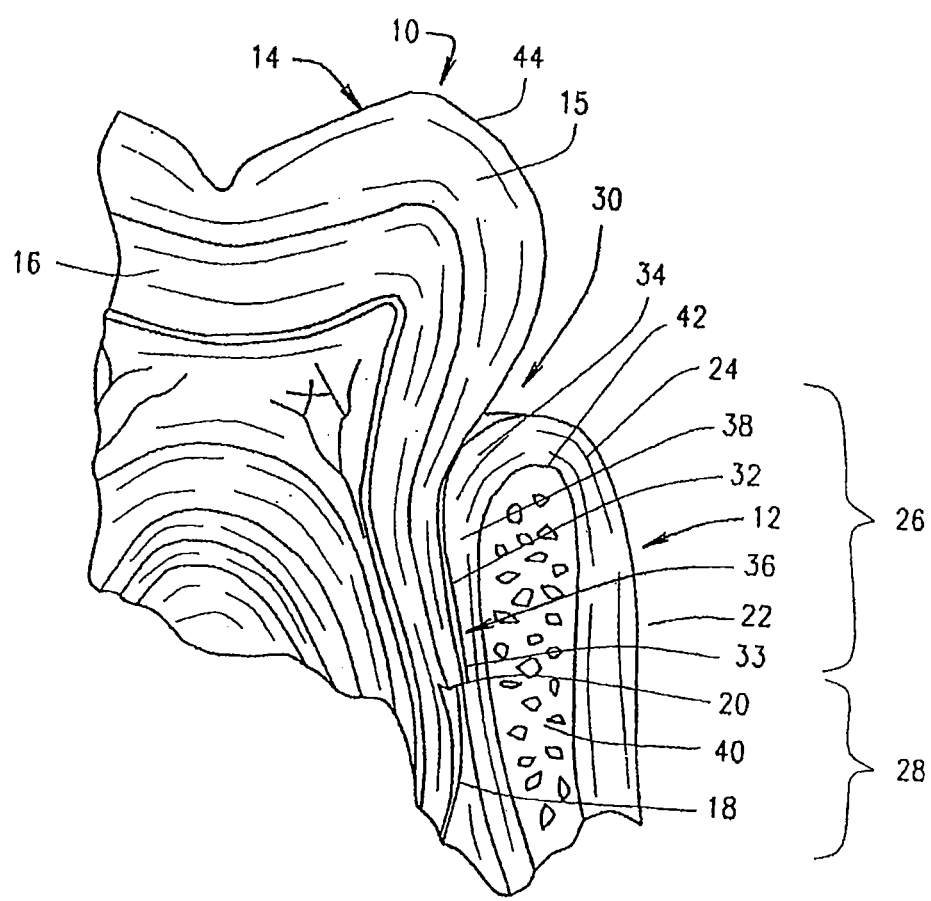
FIG. 1 is a cross-sectional view of a healthy tooth and gingival tissue.
Figure 2A:
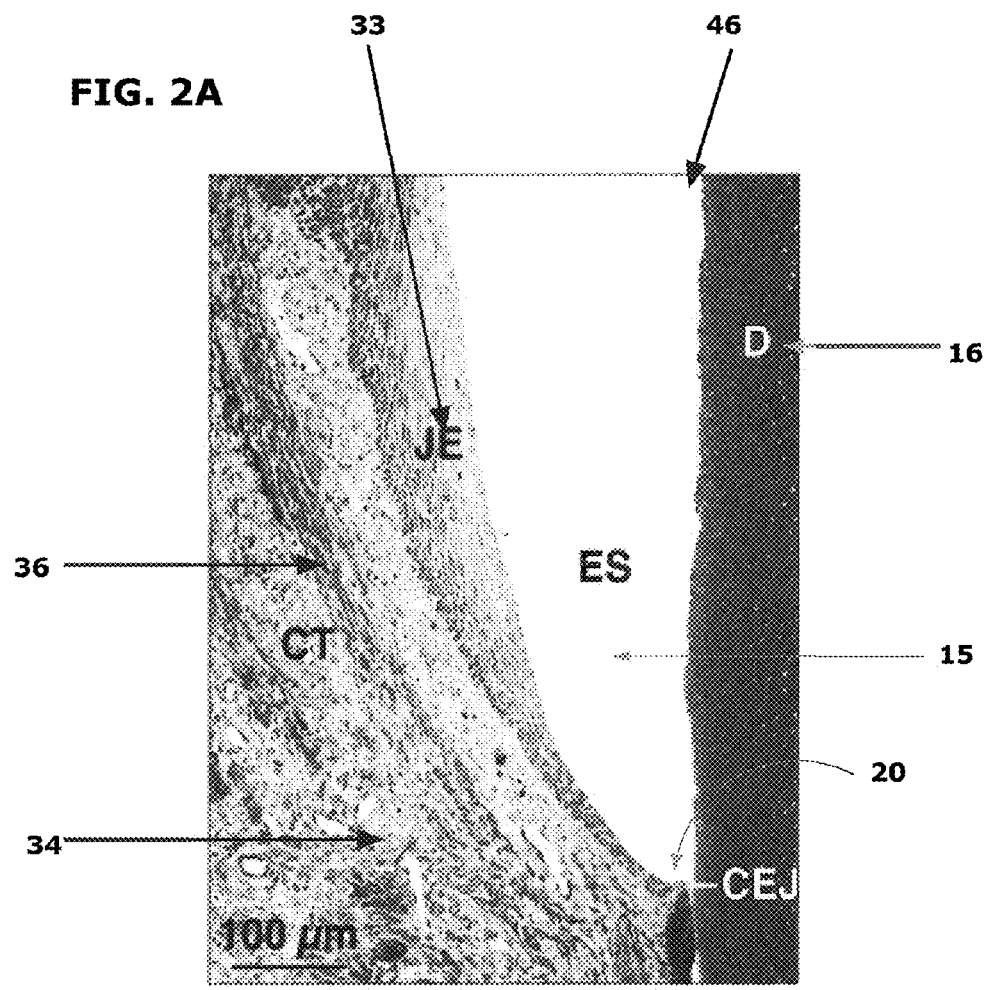
FIG. 2A is a cross-sectional close-up photographic image of a marginal gingiva and tooth structure including a cementoenamel junction.
Figure 2B:
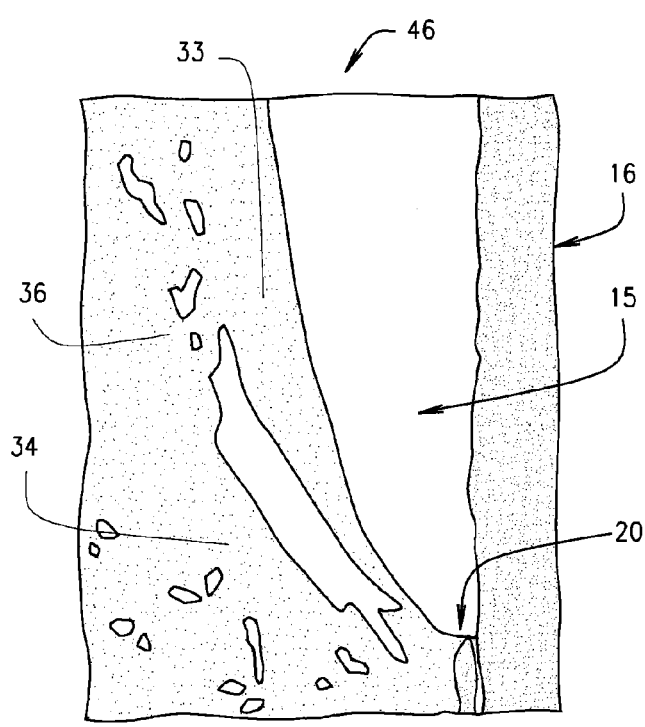
FIG. 2B is a line drawing representation of the photographic image of FIG. 2A.
Figure 4A:
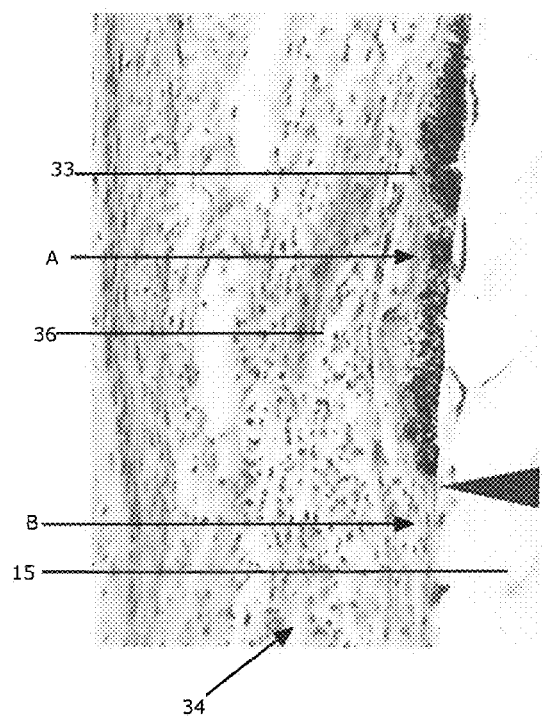
FIG. 4A is another close-up side photographic image of a tooth and associated marginal gingiva.
Figure 3A:
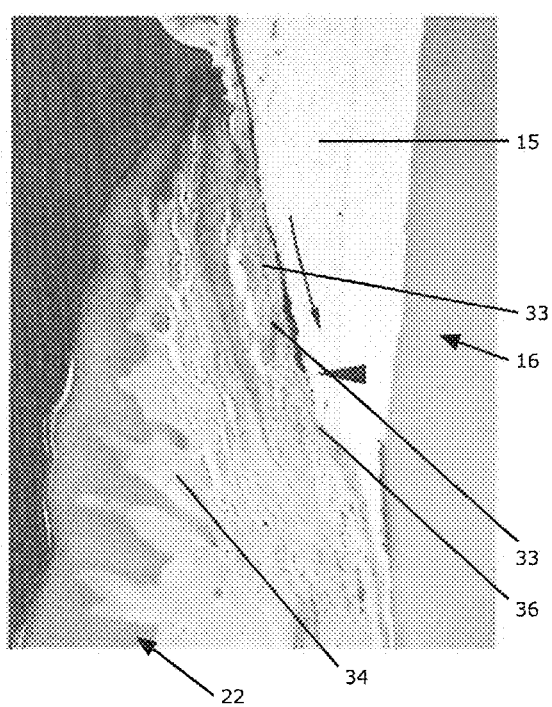
FIG. 3A is a close-up side photographic image of a tooth and associated marginal gingiva.
Figure 3B:
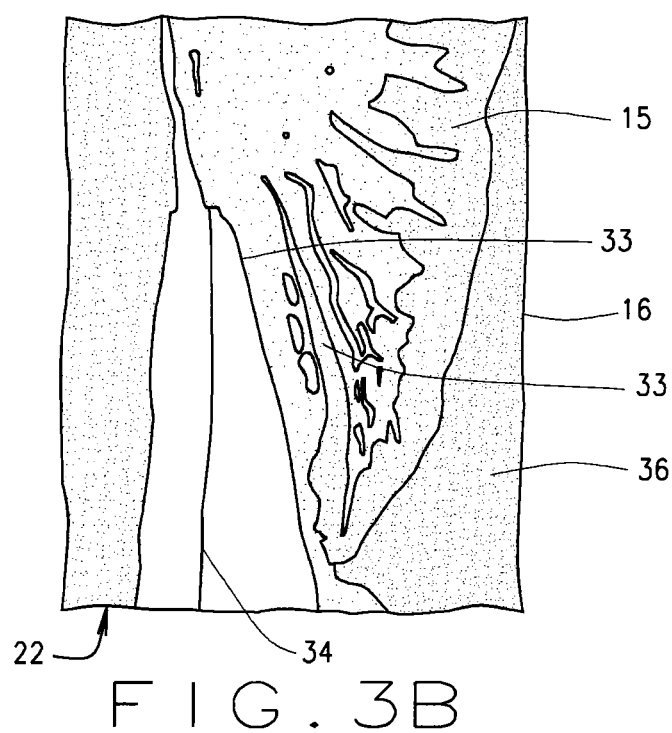
FIG. 3B is a line drawing representation of the photographic image of FIG. 3A.
Figure 4B:
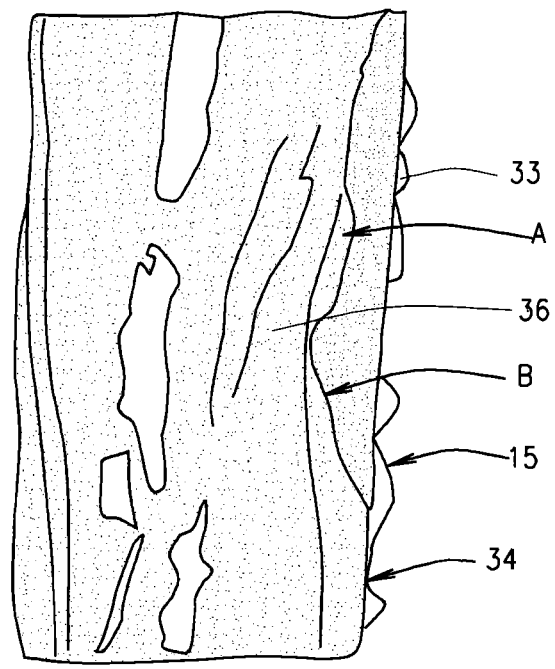
FIG. 4B is a line drawing representation of the photographic image of FIG. 3A.
Figure 5A:
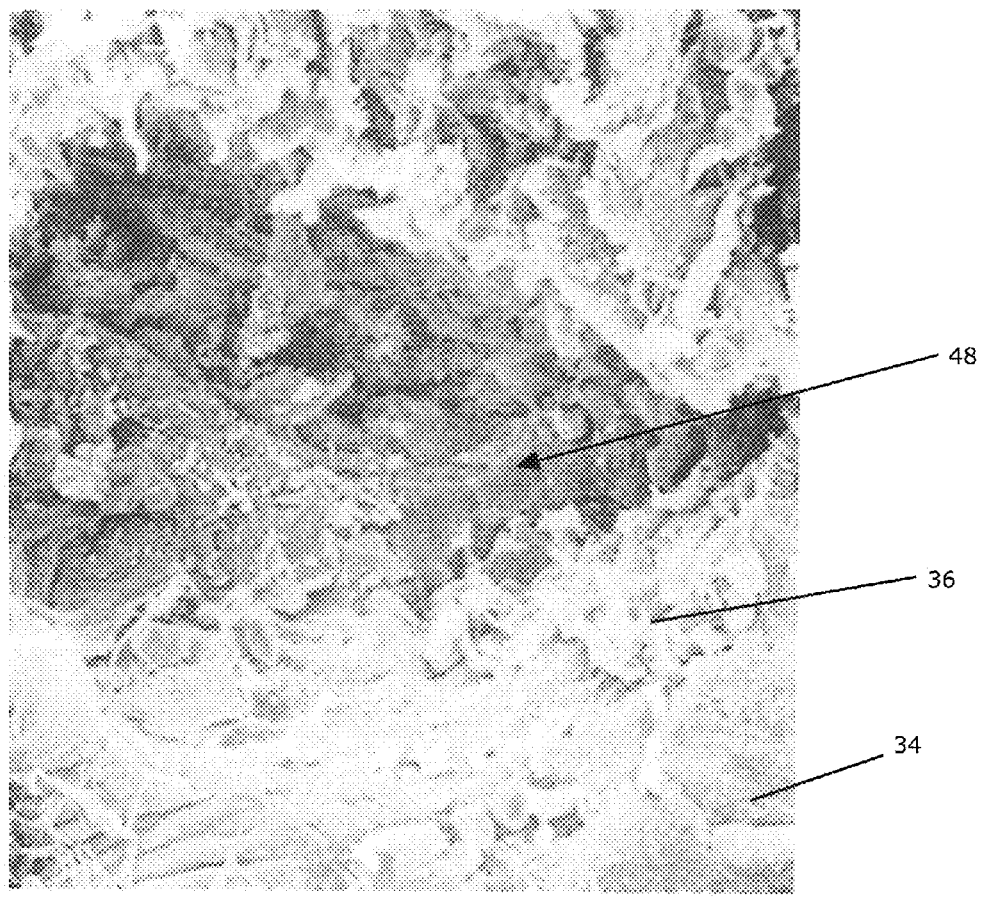
FIG. 5A is a photographic microscopic image of an ulcer in a periodontal pocket.

FIG. 1 shows a healthy tooth 10 with surrounding gum 12. The tooth 10 includes a crown 14 having enamel 15, an inner composition of dentine 16 that forms the root of the tooth 10, and cementum 18 that covers the outer surface of the lower portions of the tooth 10 below the enamel 15. A cementoenamel junction (CEJ) 20 is defined as the intersection of the lower end of the enamel 15 and the start of the cementum 18. As shown, the gum 12 includes gingiva 22 that has gingival tissue 24 having a portion referred to as marginal gingiva tissue 26, and attached gingiva tissue 28, the two portions generally being separated by the CEJ 20. The gum 12 forms a gingival sulcus 30 at the intersection with the tooth 10. An epithelium 32 covers the lower portions of the enamel 15 above the CEJ 20 such that the cementum 18 is not exposed in a healthy tooth 10 as shown. Connective tissue 34 of the gingiva tissue 24 is adjacent to the epithelium 32 (this portion referred to as the junctional epithelium 33) and includes a bed of capillaries, hereinafter referred to as a capillary bed 36, and alveolar fibers 38. An alveolar bone 40 has an alveolar crest 42 that extends nearly to the CEJ 20 to form a deep socket (not shown) for the tooth 10. Biofilm 44 generally forms to coat the outer surface of the enamel 15. FIGS. 2A and 2B illustrates a close-up of an environment 46 about the CEJ 20 including the location of the junctional epithelium 33 between the enamel 15 and the connective tissue 34 that includes the capillary bed 36.

FIGS. 3A and 3B and 4A and 4B illustrate environment 46 in additional detail. Where the epithelium 32 exists, as shown at "A" in FIG. 3B, there is only 1 or 2 cells separating the interface with the outer surfaces of the tooth 10 that can be exposed when the gingival sulcus 30 widens during infection. When the bacteria proliferate in this region, the tissue is modified so there is no epithelium 32 present as shown at "B" in FIGS. 4A and 4B. The exposure of the underlying connective tissue 34 and capillary system 36 allows for direct contact or at least very close proximity of any pathogens present in the gingival sulcus 30 or, a periodontal pocket (not shown) associated therewith. As such, there is direct access to the host circulatory system by such bacteria and thus systemic involvement is possible.

While not shown in the figures, in a diseased tooth 10 such as with one having an inflammation from periodontal disease, the junctional epithelium 32 moves apically (or toward the apex of the root), exposes the cementum 18, and enlarges the sulcus 30 thereby creating a pocket (not shown). Facultative anaerobes modify this environment 46 from one with minimal oxygen to an anaerobic environment conducive to development of virulent anaerobic periopathogens. An ulcer 48, such as shown under magnification in FIGS. 4A and 4B, can form in the periodontal pocket. As can be seen in this illustration, the ulcer 48 of the periodontal pocket can be directly adjacent to, and/or in contact with the capillary bed 36 of the connective tissue 34. As the inflammation spreads, the alveolar bone 40 is destroyed. This increases the mobility of the tooth 10 and can lead to loss of the tooth 10. Additionally, this enlarging reservoir (enlarged sulcus 30 and pocket) serves as a source of bacteria, bacterial products, and host inflammatory responses that can become systemically involved via the close proximity to the host bloodstream.

In one embodiment, a method of treating and controlling oral periopathogens includes performing an evaluation examination of a patient. The evaluation exam includes evaluating one or more treatment regions having potential periopathogens. Each such treatment region is individually evaluated as, with the present method, a different periopathogen that can be determined in different treatment regions. The inventor hereof has determined that prior practice of assuming the same or a common periopathogen is flawed as different pathogens can exist in different regions and can require different treatments and different medicaments. As provided by this method, a bacteria or bacterial community is determined for each treatment region and a biofilm for each treatment region is also determined. Each combination of bacterial and biofilm can be referred to as the biofilm community as described above. As will be addressed in further detail below, the identification of the biofilm community enables the individual biofilm bacteria being identified for selection of the medication to control the pathogens and to ensure that the medication is selected to adequately penetrate the particular biofilm.

The evaluation examination can include taking one or more cultures for each of the treatment regions and evaluating or testing each culture by a suitable identification technique. Such can include DNA analysis and/or PCR analysis, or other diagnostic and testing methods and systems that are capable of determining the bacteria and biofilm present to a desired degree of certainty and specificity. Such determination can also include determining each bacteria that is present sub-treatment regions including a subgingival biofilm and/or a gingival tissue associated with a subgingival biofilm.

In some embodiments of the present method, samples from the various periodontal pockets of a patient are obtained by an attending medical care provider, such as a dentist. Each of these samples is identified as to the site from which they were obtained. Each sample is obtained and retained for analysis or determination of the bacterial community and/or biofilm present in each periodontal pocket. For instance, this may require, in some instances the obtaining of the tissue sample such as to preserve or protect the sample. This can require, for example in the case of a virulent bacteria, including anaerobic bacteria, that cannot grow when exposed to air, the extraction of the sample in a continuous enclosed and protected manner, as is known in the art or as may be developed for this purpose. In another example, new methods and techniques may be required so as to provide the bacteria in the sample appropriate or varied culture media in which to grow. This may include, at least in part or as an option, an alternative to the conventional culture media that may include bacteria waste product samples, by way of example. Generally, the sampling method and devices should be configured for ensuring that the samples, once extracted, can be maintained, to accurately determine their bacterial community and/or biofilm. While DNA testing is generally known, the present methods apply DNA or related testing in a manner that, heretofore, has not been utilized and for which no prior purpose has been identified, in the absence of the method as described herein.

Based on the determinations, the initial treatment regions can be combined or new treatments regions delineated, such as by subdividing the initial treatment regions. For example, in performing multiple cultures of a first initial treatment region, it may be determined that one portion of the treatment region has a first bacteria and biofilm and that a second portion of the same treatment region as a second bacterial and/or biofilm, wherein at least one of the bacteria or biofilm is different. In such case, the initial treatment region may be subdivided so that each treatment region can be treated with a targeted and specific medicament.

The method includes preparing a periodontal medicament delivery tray for the patient wherein the delivery tray has one or more application regions and can have one or more tooth indentations that aid in the receiving of medicaments and the delivery of the medicaments to desired specific and differentiated treatment regions so as to target the delivery of selected medicaments for treatment of the specific bacteria within the biofilm as determined for each treatment region. The periodontal medicament delivery tray therefore will be prepared so as to include delivery regions that are specifically matched to the desired treatment regions. As described herein, a periodontal medicament delivery tray may be one that is capable of delivering the selected medicament to each treatment region, such as periodontal pockets associated with each tooth, and maintaining the medications in the treatment region for a sufficient period of time so as to effectively treat the bacteria within the biofilm. One example, of such is the Perio Tray™ as described in U.S. Pat. No. 6,966,773, as issued to the inventor hereof. As described herein, such periodontal delivery trays, or variations thereof, can be worn by the patient for the purpose of controlling the oral periopathogens that are associated with specific systemic disease factors and conditions. Referring to FIGS. 6, 7 and 8, a form-fitted flexible periodontal medicament delivery tray 50, is adapted for applying one or more of the medicaments 52 described in the various methods in accordance with various embodiments. More specifically, tray 50 is of a suitable soft plastic elastomeric or other suitable material which is molded in place to the patient's teeth so as to form a dental arch recess 54 which conforms closely to a patient's teeth and which firmly and closely fits in place on the patient's teeth. A raised seal 53 in a location such that a resilient material is formed as a seal 53 against the patient's adjacent gums. The seal 53 is formed with minimal contact to the patient's teeth, but in a manner to direct medicaments into each of the treatment regions, such as the sulcus or periodontal pocket that can be the source of an oral infection. Tray 50 is shown to be a full arch tray, but those skilled in the art will recognize that a partial arch tray or a dual arch tray may be used, if desired.

It should be noted that the application of the medicament can be performed in any suitable manner that may be equivalent to the delivery tray. When the delivery tray is used, a tray is adapted for directly applying a medicament to the gums about the teeth, the gingival tissue, is used. For example, the medicament can be filled or at least partially filled into a cavity of periodontal medicament delivery tray. The tray can then be attached or applied to the gums and about the associated teeth for application of the medicament to the area to be treated. Additionally, as shown in FIG. 6, in a region where there is only a single tooth and/or treatment region, only one of the upper or lower teeth and associated gingival tissue will be treated. In the alternative, where both the upper and lower teeth include one or more treatment regions, as shown in FIG. 7, both the upper and lower teeth and associated gingival tissue can be treated simultaneously.

Based on the determination of the bacterial and biofilm in each treatment region, the method provides for selecting a medicament to be applied to each treatment region from among a plurality of potential medicaments. The selection process is tailored to selecting the most appropriate medicament for each treatment. The medicament is selected from among the potential medicaments based on each medicament that can be a single medicament or a combination of medicaments, herein both referred generally to as a medicament that is capable of controlling the bacteria within each associated biofilm.

Specific medicaments, whether individual medicaments or combination medicaments, i.e., a medicament that is composed of a plurality of medications, are selected based on their ability to control specific biofilm bacteria such as having an efficacy against further growth or that can kill existing bacteria. Additionally, the medicament is selected at least in part on the medicaments ability or capability on penetrating the biofilm present with the bacteria. The medicament is selected to be applied to those treatment regions where the specific microbes or bacteria are found within the specific determined biofilm so as to best control the pathogen population therein. The site-specific medicament can be modified as alterations or changes in the biofilm matrix are determined by further or continued or repeated analysis, such as by PCR or DNA analysis or other suitable means or methods, of the bacteria community and/or biofilm within each treatment region.

The plurality of medicaments can include, but is not limited to, an antimicrobial agent, an oxidizing agent, an antibiotic agent, and an interferon, by ways of example. Colloidal gels can also be applied including, but not limited to, by way of examples, Perio Gel from Perio Pharma, Peroxyl from Colgate Palmolive, and Carbamide peroxide gel.

The method also provides for applying each of the selected medicaments to each appropriate treatment region. This typically provides for the placing a selected medicament in each application region of the delivery tray associated with each treatment region for targeting the applying of each medicament to each determined bacteria in each determined biofilm. As noted, in subsequent evaluations after beginning of the method as described herein, it may be determined that one or more bacteria is present that are symbiotic of a commensal biofilm. Where such a situation, a maintenance medicament can be selected from among the plurality of potential medicaments that can be applied to maintain the desired environment. The maintenance medicament is selected as a function of determining the maintenance medicaments ability to promote an aerobic environment conducive to a propagation of the harmonious bacteria in the one particular treatment region. The method provides for the application or delivery of each selected medicament, into each of the associated periodontal pockets and maintained in the pocket for a prescribed period of time sufficient to treat the periopathogens with a sufficient efficacy of the selected medicament. As one example, the medicament is selected so as alter the environment from one conducive to disease (anaerobic) to one conducive to health (aerobic). In some embodiments, such the selected medicament is applied using a periodontal medicament delivery tray available to the patient or as procured during the first step, where applicable. Examples of medicaments include, but are not limited to, antimicrobial agents including Actisite, Atridox, Periochip, Arestin, Perio Tray™/colloidal hydrogen peroxide, Electrolyzed water, Alcohol, Iodine, and Hydrogen Peroxide.

As noted, the medicaments can be selected in whole or in part, or can be modified, combined and/or customized for each determined bacterial community based on the expected efficacy of the medicament for such determined bacterial community or biofilm. Generally, any combination medicament having two or more medicaments requires that the combination of medication be evaluated and/or approved as a combination, and not merely combining of two medicaments, without the combination being separately evaluated.

For example, during either an initial diagnosis procedure of a patient or where all or a portion of an affective region fails to favorably respond to a general broad-spectrum or a antimicrobial agent or other medicament, a sample of the bacteria within the periodontal pocket is obtained and forwarded to a lab for determining the particular periopathogen or periopathogens present in each of the treatment regions. A sample can be taken from an attending medical practitioner by using any suitable means, including, by way of example, a paper point inserted into the periodontal pocket to be tested. After the diagnostic procedure is completed and the particular bacteria or biofilm present in each of the periodontal pockets or treatment regions is determined, a medicament is selected or customized, such as by creation of a blend or cocktail of agents or medicaments, for specifically controlling the determined bacteria within the biofilm. Such a process can be initiated at the beginning of a treatment as described herein, or can be performed during or with one or more of the other processes to aid in the overall treatment of the patient.

In some embodiments, the patient can deliver the selected medicament or medicaments in a manner such that the particular medicament selected for a particular treatment region to treat a particular determined periopathogen or biofilm in that treatment region is provided only to that region to continue to manage the affected environment to kill or continue to kill the obligate and facultative anaerobes and/or prevent their formation in a general or a site specific manner. The application of the selected medicament beneficial to health can be provided as a long term treatment of which the patient self-applies at home. It can also be extended as needed to control any chronic aspects of the periodontal disease and to maintain an environment conducive to health that is aerobic and further inhibits the growth and re-growth of anaerobic bacteria.

The applied medicament can be any selected medicament that is suitable for managing the microorganisms and for maintaining a tissue environment that is conducive to health. This can be a medicament that is aerobic and inhibits the growth and re-growth of anaerobic bacteria or any other medicament conducive to a favorable and healthy situation. For example, this can include, but is not limited to hydrogen peroxide. Of course, it should be understood that the application of the medicament can be a single application or can be multiple applications that can be generally delivered or site specifically delivered that are repeated more than once and can, in some embodiments, be repeated on a periodic basis. Additionally, such application of the medicament can be provided several times each day or otherwise adjusted to the frequency as may be directed or performed by a dentist or health care professional.

Following or during the current method of treatment, the method can also provide for the removal of imbedded anaerobic bacteria from the gum and/or affected connective tissue. Certain of the oral bacteria possess the capability of host cell invasion directly and cause the host cells to act in ways different from normal non-infected cells. These abnormal cells can be removed by any suitable procedure including surgery such as electro-surgery, scaling and root planning laser surgery or conventional "cold steel" surgery or any other means available for removing imbedded micro-organisms from the host cells/gum tissue. This process when applied removes the imbedded pathogenic bacteria that have the potential to invade the host cells of the host tissue. The surgical removal is often required as these imbedded pathogenic bacteria are often impervious to most other treatment methods. While such pathogenic bacteria are controlled and/or killed in the procedures of applying the selected medicament, altering the environment, and/or modifying a protein or amino acid substratum, the removal of the imbedded pathogenic bacteria is performed for providing a healthy and clean environment. Such removal can be by any suitable method, and can include physical removal such as by surgery. However, it should be noted that it has been demonstrated that subgingival bacteria remaining after conventional treatments have the potential to re-colonize to pretreatment levels if not property maintained, thus fostering the re-growth of obligate anaerobes. For example, in one known study, oral biofilm was evaluated before and after conventional periodontal therapy. Samples taken before periodontal therapy harbored more bacteria than after therapy. Samples taken after periodontal therapy had the same species as were present before treatment, but in a reduced number both sets of biofilms grew at a similar rate.

The treatments or process as described here can provide for the removal of the subgingival bacteria that remains after conventional periodontal treatments as they have the potential to re-colonize to pretreatment levels if the corrected environment is not otherwise properly maintained. The determination of the bacterial community and/or biofilm for each treatment region, the subsequent selection of the medicament for each determined bacterial community and biofilm, and the application of such selected medicaments to the corresponding treatment region, as provided by the present processes, can provide for a significant improvement of the health of the patient following conventional periodontal treatments.

Following the removal process, a medicament, such as a colloidal hydrogen peroxide gel, or suitable substitutes and equivalents, by ways of example, can be applied to the sulcus such as by using a periodontal medicament delivery tray, for example sometimes referred to herein as Perio Tray™ treatments. Examples of such available application methods include Perio Chip, Arestin, Perio Tray/Perio Gel, Atridox, and Actisite. Of course, those skilled in the art will recognize that there are other current and future suitable alternatives, each of which is considered to be within the scope of the present disclosure. Additionally, it should be understood that this process may be provided by the medical care provider as instructions to a patient for their self-care.

These treatments facilitate healing of the affected tissue by providing or continuing to maintain the modified environment and to continue to prohibit the growth of pathogenic bacteria. In this manner, the gains made in prior processes are maintained and the growth of any additional pathogenic and especially anaerobic bacteria within the gums is suppressed. This application of the medicament such as the colloidal gel and/or hydrogen peroxide gel, to the sulcus and/or periodontal pockets of each treatment region can further inhibit the development of the obligate anaerobic population within the treated environment and can foster healing of the host connective tissue. As one example, a Perio gel at 1.7 percent from Perio Pharma has been evaluated as to efficacy in management of oral periopathogens in an anaerobic environment and is one example of a suitable treatment for this process.

The scope and magnitude of the disease, the depth of the periodontal pocket and the colonization of the pathogenic and especially gram negative anaerobic pathogenic bacteria determine the frequency and duration of treatments for each treatment region of the patient. Modifications in the environment render a change in the bacterial flora and changes in the host response, which will result in a modification in the frequency and duration of medicament usage or application to each of the treatment regions, or as often also referred herein as the application regions.

The utilization of a periodontal medicament delivery tray such as the Perio Tray™ in this administration of the selected medicament to one or more of the treatment regions typically requires that the device have corresponding or more than a single delivery region. Suitable substitutes can include, but are not limited to, filling at least a portion of a periodontal medicament delivery tray (could be the same or a different one than identified above) with a first medicament such as hydrogen peroxide gel, by way of example, and attaching the tray about the gingival tissue in such a manner as to direct the medicaments to the oral biofilm. Of course it should be understood to those skilled in the art that the administering of the medicament, for example a colloidal hydrogen peroxide gel, to the gingival tissue can be repeated more than once and site-specific medications can be delivered for optimal control of certain pathogens. For example, the administering can be repeated on a periodic basis such as once or twice per day. Additionally, the administration can be provided subgingival by the patient several times each day or otherwise to adjust the general or site-specific dosage or frequency of medicament administration as may be directed by a dentist or health care professional, such as may be required in accordance with the diseased status and also changes in the status of the disease as healing occurs.

The method can also include application of a cleaning agent to the gingival tissue, gums and/or the tooth of the affected area for removal of any dead bacterial cells or the protein layer that may be present. This can be any suitable cleaning agent and use any suitable cleaning method. In one embodiment, this includes use of a sonic or ultrasonic cleaning agent using a sonic cleaning device or system that is applied to the affected area generally following the application of a colloidal medicament directly to the sulcus. The inventor hereof has found that the process of cleaning the gingival tissue following the above steps provides for an improved and more effective removal of the protein layer and the bacteria attached to this layer by the sonic cleaning agent. Additionally, this order of processes was found in some embodiments to disrupt the protein layer that improves the effectiveness of the sonic cleaning agent in removing the protein layer. Such removal can be provided before the pathogenic bacteria can repopulate the tooth surface. Additionally, the follow-up cleaning process can create a continued oxygen rich environment, for continued modifying the environment where the facultative anaerobic bacteria and the obligate anaerobes grow. In this manner, the biofilm is modified from one conducive to disease to one that is conducive to the growth of bacteria that can live in harmony with the host, e.g., commensal bacteria.

In some embodiments as described herein, the facilitation of cleaning occurs through a modification of the environment. Oral bacteria which are not able to bind to oral structures directly but require a protein, amino acid layer on which to attach. Initially aerobic bacteria colonize the region, but if the region becomes conducive to the formation of facultative anaerobic bacteria, the region can become anaerobic. One of the initial steps in treatment and cleansing must therefore be a modification of the protein or amino acid layer. This is accomplished through a timed occurrence delivery and the action of selected medicaments such as colloidal hydrogen peroxide as can permanently modify the protein layer and alter the amino acids in a permanent manner (cleaves hyaluronic acid, converts histadine to alanine and asparagine to aspartate) whereby the protein layer or amino acid layer is disrupted and is more easily removed by mechanical or sonic means.

Of course, it should be understood that the cleaning of the gingival tissue can be repeated two or more times and in one embodiment, and can be repeated following each of any repeated administering of the medicament such as a colloidal hydrogen peroxide gel. Such cleaning can be provided by the patient several times each day or otherwise to the frequency as may be directed by a dentist or health care professional. Additionally, such cleaning can be directed or provided as instructions from the medical provider to the patient for self-care.

The protein and amino acid modification alters the substrate such that mechanical and sonic cleaning agent, by way of example, a sonic toothbrush that applies a cleaning agent such as a sonic cleaning agent to the gingival tissue.

There are multiple potential cleaning agents readily available that include dentifrices, mouth rinses, tooth paste, oral irrigants and other commercial products.

As described herein, the method first begins with an examination using suitable methods to evaluate the presence and effects of periodontal disease. Additionally, the examination can be repeated throughout the treatment period and the method adjusted and repeated as treatment changes the bacteria and/or biofilm in one or more of the treatment regions. During such examination processes, the requirement of one or more medicament delivery methods and identification of treatment regions to be addressed by the delivery tray, are evaluated. The fabrication of a tray may be initiated during an early examination and prior to application of the above other processes of the method. This can be at any time prior to the remaining treatment processes. Currently such periodontal medicament delivery trays often take some time to be fabricated, especially if one is not currently available for the patient's use. However, there may be some instances where a periodontal medicament delivery tray may already be available to the patient. In such instances, this portion of the process may be skipped especially as to obtaining the impression and the fabrication of the periodontal medicament delivery tray. In some cases, as one skilled in the art will also understand the methods as described herein can be performed following or in parallel with conventional periodontal treatments such as scaling and root planning, surgery, laser surgery or localized delivery of antibiotic or antimicrobial agents to the infected area (Arestin, Perio Chip, Atridox, Actisite, etc.)

The process of preparing the medicament delivery tray, such as a Perio Tray™, the method includes fabrication of the periodontal medicament delivery tray including preparing a female impression of the patient's teeth and adjacent gums that are the affected gums, making a male model of the patient's teeth and adjacent gums from the female impression, and fabricating the tray from the male model. In one embodiment, this also includes forming a raised seal in a location such that a resilient material is formed as a seal against the patient's adjacent gums. The seal is formed with minimal contact to the patient's teeth, but in a manner to direct medicaments into each of the treatment regions, such as the sulcus or periodontal pocket that can be the source of an oral infection.

In the situation where a patient is identified as suffering of an obligate anaerobic infection (that is an organism that survives only in the absence of oxygen, e.g., obligate anaerobe) in one or more of the treatment regions, the method provides for the direct application of an aerobic colloid applied directly into the sulcus or periodontal pocket. In a situation where a patient is found to suffer with a specific pathogen dominated disease in one or more treatment region, direct medications can be delivered to that specific site to assist in controlling the infectious agent. The medicament is selected not only due to the efficacy against the particular bacteria determined to be present in the treatment region, but also based on the ability of the medicament to readily penetrate the biofilm in which the bacteria is present, i.e., the determined biofilm in the treatment region in which the bacteria is present, and therefore the site-specific biofilm matrix.

The method of direct per treatment region application can vary in accordance to the scope and magnitude of the disease, even to the point of microbial-specific medication delivery to specific sites of the infection. Gingivitis treatments usually can be rendered from one to three times a day and long-term maintenance can be obtained with daily or twice daily applications. Periodontitis treatments can be rendered from two to six times a day, modified as healing occurs and maintained with long-term usage of two or more times a day as determined by the patient's conditions and healing. Any region that requires site-specific treatment can be administered as the micro-organisms are recognized to require specific considerations. Multiple uses of the trays enables different medicaments to be delivered to a one or more treatment regions if selected medicaments are not compatible with each other if given simultaneously, and must be applied serially, or at different times.

In some embodiments, additional application of one or more medicaments generally can also be used in conjunction with the treatment region specific application of site specific medicaments. These can include, but are not limited to, oral rinses, application through brushing or flossing, direct application and through usage of the Perio Tray™ system and special microbial-specific medications. Oral rinses are not generally deliverable into the periodontal pocket as rinses are unable to overcome crevicular flow. Similarly, brushing and flossing do not typically penetrate greater than 3 mm into the periodontal pocket and even then crevicular flow dilutes the medicaments. In addition, the bacteria are so small and reproduce so rapidly that mechanical removal alone has proven ineffective in controlling them. Likewise, direct medicament applications into the periodontal pocket are unable to maintain a sufficient amount of medicament over an extended period of time and are not renewable to alter the environment and maintain a modified environment sufficient for health and healing. As such, a periodontal medicament delivery tray such as the Perio Tray™ system has been found to provide for direct application of the treatment site specific medicaments in many situations and applications. This can encompass general medicament delivery or site-specific micro-organism specific medicaments.

In some embodiments, the direct application of a medicament can create an oxygen rich environment that kills the obligate anaerobes contained therein and kills the facultative anaerobes (a facultative parasite can live independently of its usual host as they can live off the waste products of other bacteria) as well as aerobic bacteria in the associated biofilm. This includes killing facultative anaerobes including bacteria that can live in both aerobic and anaerobic environments. By killing the facultative anaerobes, they are prevented from modifying the environment to one where the most virulent obligate anaerobes are able to function. As such, this process that includes identifying and killing these facultative anaerobes in the biofilm in addition to the then present obligate anaerobes (including those that cause decay) can provide for inhibiting the future growth of obligate anaerobes in addition to killing those currently present. It would also be possible to introduce specific beneficial bacteria into the regions as healing occurs to compete with the pathogenic bacteria and promote healing and a healthy environment.

A medicament, such as a specific antimicrobial agent for the identified bacteria, by way of example, can in some situations be limited to treatments where there is an acute infection. As such, the administering of the specific antimicrobial agent for the identified biofilm can be provided in the acute phase treatments to address the virulent pathogens and to change the environment from one conducive of virulent pathogen development to one that is not conducive thereof. It is also understood that site-specific micro-organism-specific medications could be used as deemed appropriate by the health care provider.

It should also be understood that the above processes can be practiced once or can be repeated two or more times as may be needed or desired to obtain the desired effects for each identified treatment region and each determined bacteria in each biofilm. It should also be understood that such direct application of a medicament can be provided by the health care provider or by the patient several times each day or otherwise adjust to the frequency and length as may be directed by a dentist or health care professional. It is also possible to introduce commensal bacteria into the sulcus or periodontal pocket by direct application means.

The methods and systems as described herein address the pathogens in a synergistic approach that provides steps that collectively have improved benefits over current practice and procedure. Control of the pathogens in the periodontal pocket and maintenance of a pathogen free environment manage the introduction of these organisms into the host circulatory system. This oral/systemic control has important medical implications.

Literature in the medical and dental journals demonstrate that being able to control oral periopathogens have effects on systemic situations. Various embodiments of the present systems and methods can provide for the control of oral periopathogens on a per-treatment region as it is recognized that each treatment region that contains the bacterial periopathogen can individually and combined negative effects on systemic situations, for example, controlling the oral periopathogens decreases C-reactive protein and lower patient lipid levels, decreases patients glycosylated hemoglobin and decreases the incidence of premature and low birth weight babies.

Additionally, the inventor hereof has also documented using a scanning electron microscopy that the periopathogens can be reduced by 99.98% within 12 to 17 days of the start of the treatment as described herein. These results can continue to control the periopathogens long-term in patients who use of the methods as described herein.

Patient's C-reactive protein systemic levels have been shown to decrease when the oral periopathogens are treated with the system and oral methods as described in this present disclosure. Controlling the oral periopathogens is expected that other systemic markers changes will result from the resulting control of the periopathogens.

This can provide the benefit over the prior practices and methods as some embodiments of the current method can provide for controlling one of the causes of systemic inflammation, thereby controlling systemic improvements in a patient. In addition, in various embodiments the control of the bacteria that causes decay can decrease the incidence of new or recurrent decay and site-specific medication applications are possible when needed.

As used herein, a biofilm is intended to refer to any complex structure of a mixed bacterial colony adhering to surfaces that are regularly in contact with oral structures consisting of colonies of bacteria and usually other microorganisms such as yeasts, fungi, and protozoa that secrete a mucilaginous protective coating in which they are encased. These biofilms can form on solid or liquid surfaces as well as on soft tissue in living organisms, and are typically resistant to conventional methods of disinfection. Dental plaque is an example of a biofilm. Biofilms are generally pathogenic in the body, causing a host of systemic diseases.

An anaerobe as used herein is an organism, such as a bacterium that can live in the absence of atmospheric oxygen, i.e., does not require air or free oxygen to live. Pathogenic bacteria as used herein defines any microorganisms that reside in a parasitic or harmful manner and causes infectious, injurious, inflammatory or other deleterious effects on the host. Additionally, while bacteria such as anaerobic bacteria are described in this disclosure, such reference is by way of exemplary embodiment. It should be understood that such references to bacteria can similarly include or alternatively apply to micro-organisms, wherein micro-organisms are fully within the scope of the present disclosure.

As used herein, commensal refers to a symbiotic relationship in which one species is benefited while the other is unaffected or an organism participating in a symbiotic relationship in which one species derives some benefit while the other is unaffected.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A method of treating and controlling oral periopathogens, comprising:
    performing an evaluation examination of a patient including evaluating two or more treatment regions of the patient on a common arch containing a plurality of teeth having potential periopathogens, each treatment region having at least one tooth on the common arch and determining a bacterial community having one more identified bacteria and a biofilm present in each treatment region;
    preparing a periodontal medicament delivery tray for the patient for two or more teeth of the common arch, the delivery tray having two or more medicament specific and differentiated application regions each including one or more tooth indentations, each application region being matched to a different one of the treatment regions and configured for applying at least one of two or more medicaments to the matched different one of the specific and differentiated treatment regions of the common arch, each application region being separate from another one of the different application regions to target medicament delivery therein, with each application region including each tooth of each matched different treatment region;
    selecting a particular medicament to be applied to each of the treatment regions from among a plurality of potential medicaments, selecting including at least one antimicrobial medicament as a function of the at least one antimicrobial medicament's capability penetrating the determined biofilm and inhibiting further growth or killing of at least one bacteria within the determined bacterial community as determined to be in each treatment region, wherein at least two of the particular selected medicaments for two different treatment regions include a different antimicrobial medicament;
    placing each selected particular medicament in a different one of the matched specific and different application regions of the delivery tray associated with a different one of the two or more particular treatment regions for which the medicament was selected; and
    applying the periodontal medicament delivery tray on the common arch and about the teeth of the common arch of the patient with each of the two more selected particular medicaments being applied to a separate and different treatment region during the applying.

2. The method of claim 1 wherein performing the evaluation examination includes taking one or more cultures, each associated with at least one of the treatment regions.

3. The method of claim 2 wherein performing the evaluation examination includes a suitable identification technique.

4. The method of claim 3 wherein the suitable identification technique includes a technique selected from the group consisting of a DNA analysis and a PCR analysis.

5. The method of claim 1 wherein performing the evaluation examination includes determining a bacteria present in at least one of a subgingival biofilm and a gingival tissue associated with a subgingival biofilm.

6. The method of claim 1 wherein selecting a particular medicament includes selecting a first particular medicament as a function of an efficacy of the first particular medicament to penetrate a first biofilm determined to be present in a first treatment region and selecting a second particular medicament as a function of an efficacy of the second particular medicament to penetrate a second biofilm determined to be present in a second treatment region.

7. The method of claim 1 wherein each selected particular medicament includes two or more of the plurality of medicaments.

8. The method of claim 1 wherein one or more of the applied particular medicaments includes two or more of the plurality of potential medicaments the combination of which is capable of penetrating the determined biofilm and inhibiting further growth of the determined bacterial community or killing bacteria of the determined bacterial community associated with a particular biofilm present in a particular treatment region.

9. The method of claim 1 wherein the selecting includes, in addition to the particular selected antimicrobial medicament selecting one or more medicaments from the group of medicaments that are effective against the determined bacterial community within the determined biofilm consisting of an oxidizing agent, an antibiotic agent, and an interferon.

10. The method of claim 1 wherein the performing an evaluation examination is a first performing of an evaluation examination, selecting a particular medicament to be applied to each of the treatment regions is a first selecting a particular medicament to be applied to each of the treatment regions, and the applying the selected particular medicament to each treatment region is a first applying of first selected particular medicaments to each region, defining a first treatment, the method, further comprising, following the first treatment, providing a second treatment including performing a second evaluation exam of the same teeth of the common arch of the patient and a second determining of second bacterial community present and a second biofilm in each of the two or more treatment regions of the first treatment, a second selecting of a second particular medicament for each of the treatment regions as a function of the capability of penetrating the second determined biofilm and inhibiting further growth of the determined second bacterial community as determined in the second evaluation, and applying the second selected particular medicaments to each of the corresponding treatment regions.

11. The method of claim 1 wherein applying each of the two or more different selected particular medicaments to each different treatment region is repeated for a predetermined number of applications.

12. The method of claim 11 wherein performing an evaluation examination is repeated as a second evaluation that follows one or more of the applications of applying, said evaluating including determining an efficacy of the application of the particular medicaments in penetrating the determined biofilm and in reducing one or more bacteria within the determined bacterial community of the one or more of the treatment regions.

13. The method of claim 12 wherein the second evaluation examination includes determining a second bacterial community and second biofilm present in each treatment region, further comprising selecting a second particular medicament following the second evaluation examination, the second selecting including selecting at least one antimicrobial medicament as a function of the second at least one antimicrobial medicament's capability of penetrating the determined second biofilm and inhibiting further growth or killing of the determined second bacterial community.

14. The method of claim 12, wherein performing the second evaluation examination includes determining a change in the bacterial community in one particular treatment region from that determined in the first evaluation examination.

15. The method of claim 14, further comprising:
in performing the second evaluation determining one or more bacteria including determining a bacteria that is symbiotic of a commensal biofilm within the determined one particular treatment region having the change;
where a bacteria that is symbiotic of a commensal biofilm is determined, selecting a maintenance medicament from among the plurality of potential medicaments responsive to the determined change in the bacterial community and the determined symbiotic bacteria of a commensal biofilm, the selecting of the maintenance medicament for the determined one particular treatment region being a function of determining the maintenance medicament's ability to promote an aerobic environment conducive to a propagation of a harmonious bacteria in the one particular treatment region; and
applying the selected maintenance medicament to the determined one particular treatment region having the change in the bacterial community.

16. The method of claim 1 wherein placing the periodontal medicament delivery tray with the placed medicaments onto each treatment region with the matched application regions being placed about the teeth of the associated treatment regions includes attaching the delivery tray about a gingival tissue of the common arch of the patient containing the two or more treatment regions.

17. The method of claim 1 wherein preparing the delivery tray is initiated during the performing of the evaluation examination.

18. The method of claim 1 wherein applying each selected particular medicament includes providing the patient with the two or more particular medicaments selected for each different two or more treatment regions and instructing the patient to place the medicaments within each specific and different application region of the delivery tray associated with the matched different treatment region for which the particular medicament was selected and attaching the delivery tray about the treatment regions.

19. The method of claim 1, further comprising determining the efficacy of one or more of the potential medicaments including said at least one antimicrobial medicament against said one or more bacteria of the determined bacterial community as well the capability to penetrate the determined biofilm, wherein the selecting the particular medicament for each region is a function of the determined efficacy.

20. The method of claim 1 wherein selecting includes, in addition to the particular selected antimicrobial medicament selecting one or more medicament selected from the group consisting of antifungals and antivirals.

21. The method of claim 1 wherein the applying the selected particular medicaments to the common arch and teeth containing the two or more treatment regions is a plurality of applications, and further comprising evaluating the effectiveness of the plurality of applications following one or more of the applications to determine whether one or more of the treatment regions has been modified from one that is conducive for pathogen growth to one where a symbiotic bacteria of a commensal biofilm can grow.

22. The method of claim 21, further comprising determining one or more symbiotic biofilm of commensal biofilm, wherein evaluating the effectiveness of the plurality of applications includes determining whether at least one of
one or more of the treatment regions has been modified from an anaerobic environment to an aerobic environment, and
there is a presence of a condition that is favorable to the determined symbiotic bacteria of the commensal biofilm.

23. The method of claim 1 wherein preparing the delivery tray includes fabricating the delivery tray including:
preparing a female impression of a patient's teeth and adjacent gums associated with the oral biofilms being treated;
making a male model of the patient's teeth and adjacent gums from the female impression;
forming raised seals in a location such that a resilient material is formed as a seal against the patient's adjacent gums; and
fabricating the delivery tray from the male model to include the two or more different matched application regions, the fabricating including forming said raised seals about the gum line with the raised seals having minimal contact to the patient's teeth, the raised seals forming the two more specific and differentiate treatment regions of the delivery tray for directing a specific one of the selected medicaments into a specific and differentiated one of the two or more treatment regions, each of which is differentiated from another one of the two or more different matched application regions for separately containing a different selected particular medicament.

24. The method of claim 23 wherein fabricating the delivery tray further includes forming the raised seal in a location such that a resilient material is formed as a seal against the patient's adjacent gums.

25. The method of claim 1, further comprising introducing colonization of the sulcus or periodontal pocket with a symbiotic bacteria of commensal biofilm.

26. The method of claim 1 wherein the applying the selected particular medicaments to each region includes filling at least a portion of said periodontal medicament delivery tray with the antimicrobial agent and attaching the delivery tray about gingival tissue associated with one or more of the treatment regions, wherein applying the particular medicaments to each region provides for altering an environment associated with a pathogenic subgingival biofilm from anaerobic to aerobic and modifying a protein or amino acid substratum associated with a subgingival biofilm in a substantially irreversible manner in each region.

27. The method of claim 1 wherein the applying the selected particular medicaments to each region includes filling at least a portion of said periodontal medicament delivery tray with the antimicrobial agent and attaching the delivery tray about gingival tissue associated with one or more of the treatment regions, wherein applying the selected particular medicaments to each region provides for altering an environment associated with a pathogenic subgingival biofilm to one conducive to a presence of a desirable biofilm agent and modifying a protein or amino acid substratum associated with a subgingival biofilm in a substantially irreversible manner in each region.

28. A method of treating and controlling oral periopathogens comprising;
   determining a bacterial community having one or more identified bacteria and a biofilm present in each of two or more different oral treatment regions of a common arch of a patient, each different oral treatment region including at least one tooth of the common arch;
   preparing a periodontal medicament delivery tray for the patient, the delivery tray having two or more specific and different application regions each including one or more tooth indentations, the preparing including forming raised seals about the gum line with the raised seals having minimal contact to the patient's teeth, the raised seals defining and differentiating the two more specific and differentiate treatment regions of the delivery tray for directing a specific selected medicaments into a specific one of the two or more treatment regions of the common arch during use, each application region being matched to a different one of the treatment regions and configured for applying and directing one or more medicaments to a different one of the matched specific and differentiated treatment regions, each application region being separate from another one of the different application regions, with each application region including each tooth of each matched different treatment region;
   selecting a particular medicament to be applied to each of the different treatment regions from among a plurality of potential medicaments, the selecting including selecting at least one antimicrobial medicament as a function of the at least one antimicrobial medicament's capability of penetrating the determined biofilm and having an efficacy against the determined bacterial community in each corresponding oral treatment region, and wherein at least two of the particular selected medicaments for two different treatment regions are different medicaments; and
   applying the selected particular medicaments to each corresponding matched treatment region including placing the selected particular medicaments in each matched application region of the delivery tray corresponding to the oral treatment regions for which the selected particular medicament was selected based on efficacy against the determined bacterial community and penetration of the biofilm for that treatment region.

29. A method of treating and controlling oral periopathogens, comprising:
   performing an initial evaluation examination of a patient including identifying different first and second periopathogen treatment regions on a common arch of a patient, each of the two different treatment regions and having at least one tooth on the common arch and determining a bacterial community having one more identified bacteria and a biofilm present in each of the first and second treatment regions;
   preparing a periodontal medicament delivery tray for the common arch of the patient to include a medicament specific and differentiated application region for each of the two identified different treatment regions, each of the two application regions being defined by a raised seal about the gum line formed for directing an application site specific medicament within each separate and different application region;
   selecting a first particular medicament to be applied to the first treatment region including an antimicrobial medicament, the selecting of the first particular medicament being a function of its ability to penetrate the determined biofilm in the first treatment region and inhibiting growth or killing of at least one bacteria within the determined first bacterial community as determined to be in the first treatment region;
   selecting a second particular medicament to be applied to the second treatment region, the selecting of the second particular medicament being a function of the its ability to penetrate the determined biofilm in the second treatment region and inhibiting growth or killing of at least one bacteria within the determined second bacterial community as determined to be in the second treatment region, wherein the selected second particular medicament includes a different microbial medicament than the selected first particular medicament;
   placing the selected first particular medicament in the first application region of the tray;
   placing the selected second particular medicament in the second application region of the tray; and
   applying the periodontal medicament delivery tray to the common arch of the patient, the applying providing for the engaging of the seal for each application region engaging the adjacent gums with the first application region delivering the first selected particular medicament to the specific site of the first treatment region and the second application region delivering the second selected particular medicament to the specific site of the second treatment region.

30. The method of claim 29 further comprising, following one or more combination of steps of placing the first and second selected particular medicaments and the applying of the periodontal medicament delivery tray containing the first and second selected particular medicaments to the first and second treatment regions of the common arch,
   performing a second evaluation examination of the patient including determining a post initial treatment bacterial community with one or more identified post initial treatment bacteria and a post initial treatment biofilm present in each of the first and second treatment regions;
   selecting a third particular medicament to be applied to the first treatment region, the selecting of the third particular medicament including a third antimicrobial medicament as a function of the its ability to penetrate the determined post initial treatment biofilm in the first treatment region and inhibiting growth or killing of at least one bacteria within the determined first region post initial treatment bacterial community;
   selecting a fourth particular medicament to be applied to the second treatment region, the selecting of the fourth particular medicament including a fourth antimicrobial medicament as a function of the its ability to penetrate the determined initial post treatment biofilm in the second treatment region and inhibiting growth or killing of at least one bacteria within the determined second region post initial bacterial community, wherein the selected fourth particular medicament includes a different microbial medicament than the selected third particular medicament;

placing the selected third particular medicament in the first application region of the tray;

placing the selected fourth particular medicament in the second application region of the tray; and applying the periodontal medicament delivery tray to the common arch of the patient, the placing engaging the seal for each application region engaging the adjacent gums with the first application region delivering the selected third particular medicament to the specific site of the first treatment region and the second application region delivering the selected fourth particular medicament to the specific site of the second treatment region.

31. The method of claim 29 further comprising, following one or more combination of steps of placing the first and second selected particular medicaments and the applying of the periodontal medicament delivery tray containing the first and second selected particular medicaments to the first and second treatment regions of the common jaw, performing a second evaluation examination of the patient including identifying a post initial treatment bacteria that is symbiotic of a commensal biofilm within at least one of the two treatment regions and determining if the prior treatment caused a change in the treatment region from anaerobic to aerobic in a substantially irreversible manner;

where a bacteria that is symbiotic of a commensal biofilm is determined, selecting a maintenance medicament from among a plurality of medicaments to be applied to the at least one treatment region for which the change was determined, the selecting of the maintenance medicament being a function of determining the maintenance medicament's ability to promote an aerobic environment conducive to a propagation of a harmonious bacteria in the at least one treatment region;

placing the selected maintenance medicament in the application region of the tray associated with the at least one treatment region;

applying the periodontal medicament delivery tray to the common arch of the patient with the selected maintenance medicament engaging the adjacent gums with the application region containing the selected maintenance medicament about the at least one treatment region containing the bacteria that is symbiotic of a commensal biofilm.

32. The method of claim 29 further comprising, following one or more combination of steps of placing the first and second selected particular medicaments and the applying of the periodontal medicament delivery tray containing the first and second selected particular medicaments to the first and second treatment regions of the common jaw, performing a second evaluation examination of the patient including identifying in one of the two treatment regions a post initial treatment bacteria that is symbiotic of a commensal biofilm within at least one of the two treatment regions and determining if the prior treatment caused a change in the one treatment region from anaerobic to aerobic in a substantially irreversible manner;

where a bacteria that is symbiotic of a commensal biofilm is determined in one of the two treatment regions, selecting a maintenance medicament from among a plurality of medicaments to be applied to the one treatment region containing the bacterial that is symbiotic of a commensal biofilm, the selecting of the maintenance medicament being a function of determining the maintenance medicament's ability to promote an aerobic environment conducive to a propagation of a harmonious bacteria in the at least one treatment region;

placing the selected maintenance medicament in the application region of the tray associated with the identified one treatment region;

placing at least one of the selected first, second or third selected particular medicament in the application region of the tray not containing the placed selected maintenance medicament; and applying the periodontal medicament delivery tray to the common arch of the patient with the selected maintenance medicament engaging the adjacent gums with the application region containing the selected maintenance medicament about the at least one treatment region containing the bacteria that is symbiotic of a commensal biofilm.

\* \* \* \* \*